United States Patent [19]
Leckrone

[11] Patent Number: 5,026,366
[45] Date of Patent: Jun. 25, 1991

[54] ANGIOPLASTY CATHETER AND METHOD OF USE THEREOF

[75] Inventor: Michael E. Leckrone, Indianapolis, Ind.

[73] Assignee: Cardiovascular Laser Systems, Inc., Indianapolis, Ind.

[21] Appl. No.: 321,621
[22] PCT Filed: Dec. 2, 1986
[86] PCT No.: PCT/US86/02617
  § 371 Date: Jul. 26, 1988
  § 102(e) Date: Jul. 26, 1988
[87] PCT Pub. No.: WO88/04157
  PCT Pub. Date: Jun. 16, 1988

Related U.S. Application Data

[63] Continuation-in-part of Ser. No. 585,112, Mar. 1, 1984, Pat. No. 4,627,436.

[51] Int. Cl.$^5$ ............................................. A61B 17/36
[52] U.S. Cl. ........................................ 606/7; 606/15; 128/398
[58] Field of Search ............... 128/303.1, 305, 303.15, 128/395-398, 6; 604/101; 606/7, 14, 15, 17

[56] References Cited

U.S. PATENT DOCUMENTS

| 4,040,413 | 8/1977 | Ohshiro | 128/6 |
| 4,249,533 | 2/1981 | Komiya | 128/303.1 |
| 4,266,547 | 5/1981 | Komiya | 128/303.1 |
| 4,445,892 | 5/1984 | Hussein . | |

FOREIGN PATENT DOCUMENTS 0163502 12/1985 European Pat. Off. .
8301893 6/1983 World Int. Prop. O. ....... 128/303.1

Primary Examiner—Lee S. Cohen
Attorney, Agent, or Firm—Ice Miller Donadio & Ryan

[57] ABSTRACT

The disclosure relates to a device for use in removing undesired material, e.g., occlusion or plaque, from a duct or blood vessel within a patient's body. The device comprises a catheter adapted to be disposed within a duct and an element disposed adjacent to the distal end portion of the catheter such as a fiber optic emitting laser energy, a heated element or a knife for intersecting and releasing the undesired material. An inflatable bladder is provided for positioning the distal end portion of the catheter adjacent the inner surface of the duct to maintain the element for intersecting and releasing the undesired material adjacent thereto. The device can also include a pair of abutments disposed adjacent the distal end portion of the catheter to form a chamber adjacent the inner surface of the blood vessle afor receiving the undesired material and for preventing the escape of laser energy after it has been applied to the undesired material. One of the abutments may have reflecting or fluorescing material for relecting back laser energy through an optical receiving fiber that athe undesired material has been removed. The catheter also includes an occluding balloon to impede the flow of blood. Another embodiment comprises a housing having two lumens, one passing a translational and rotational filament and a second containing a fiber optic. Yet another embodiment of the invention comprises a catheter for boring a hole in a total occlusion of a blood vessel. In other embodiments of the invention, the catheter device may have a conically shaped nose to avoid trauma to blood vessels.

36 Claims, 8 Drawing Sheets

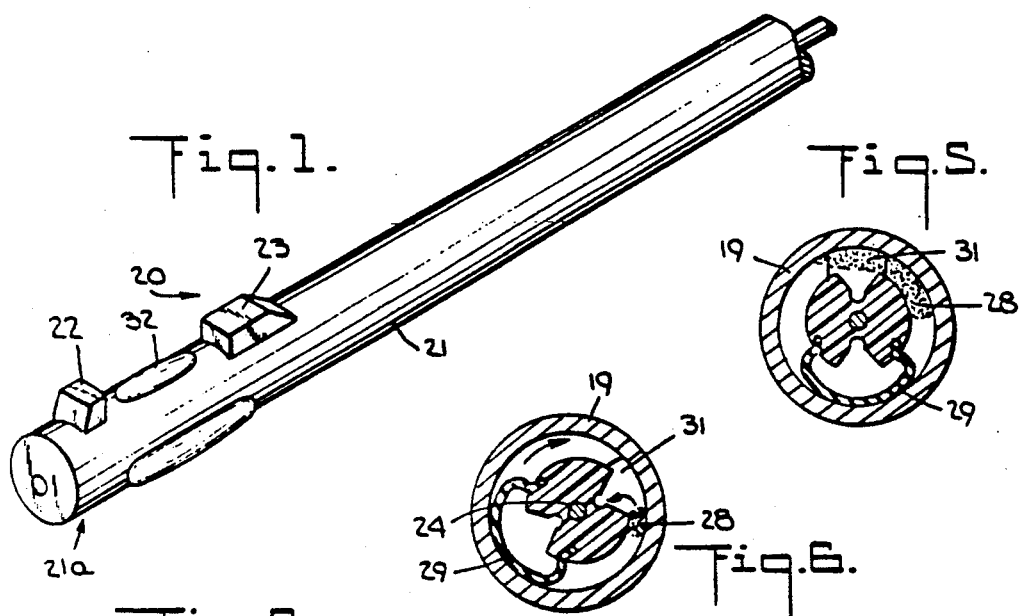
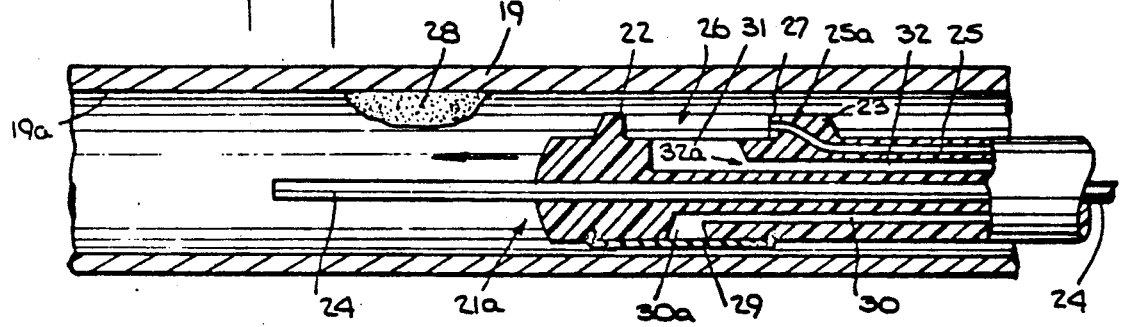
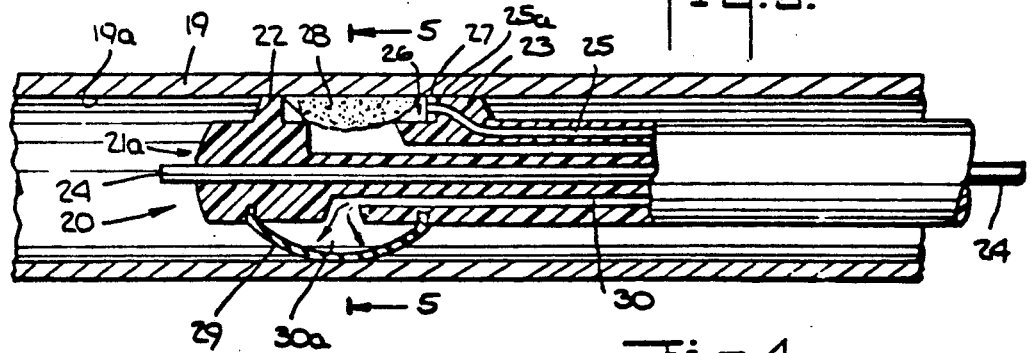
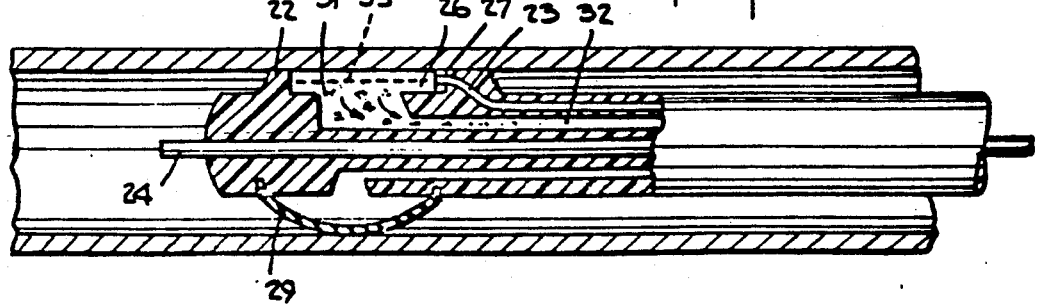

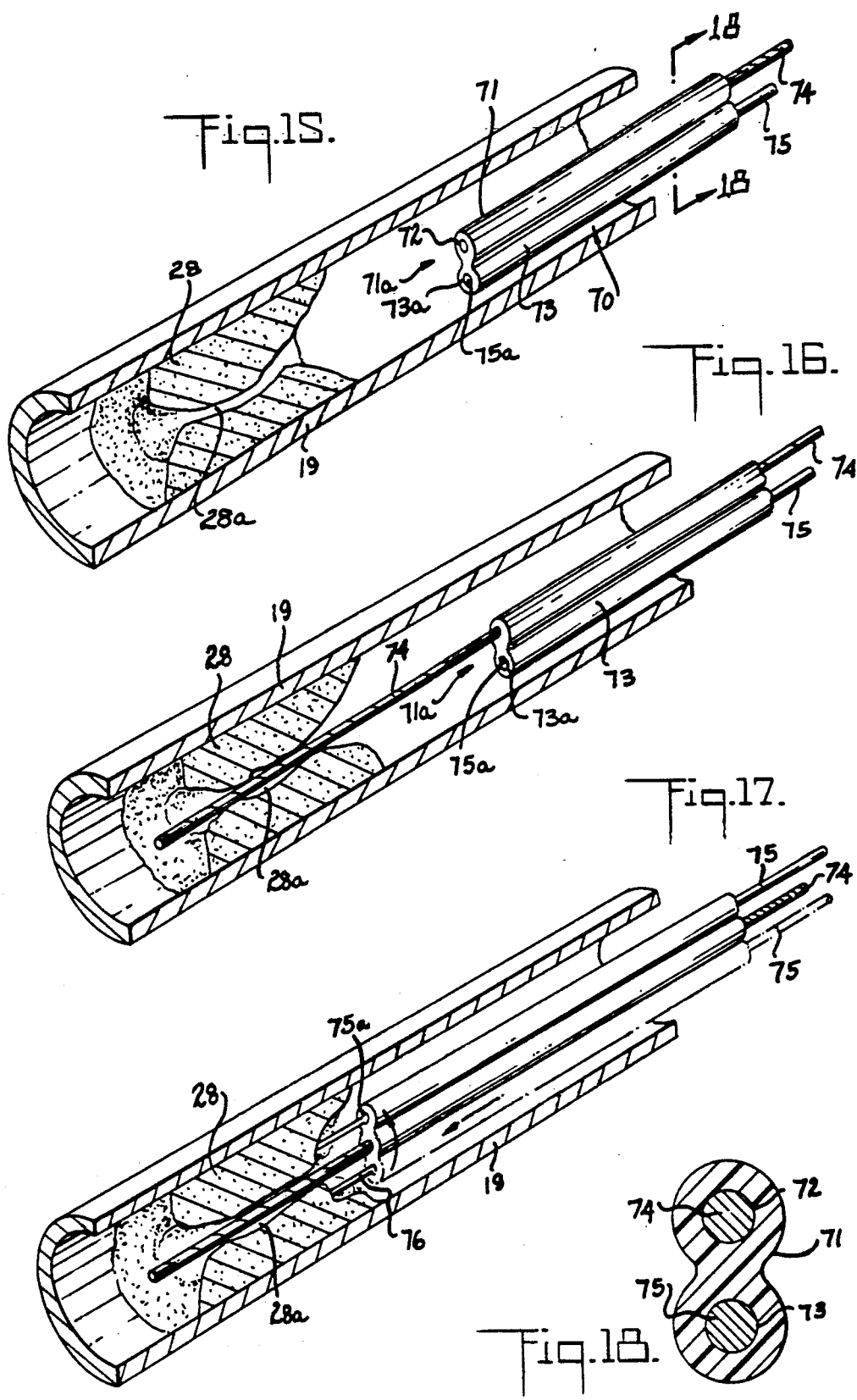

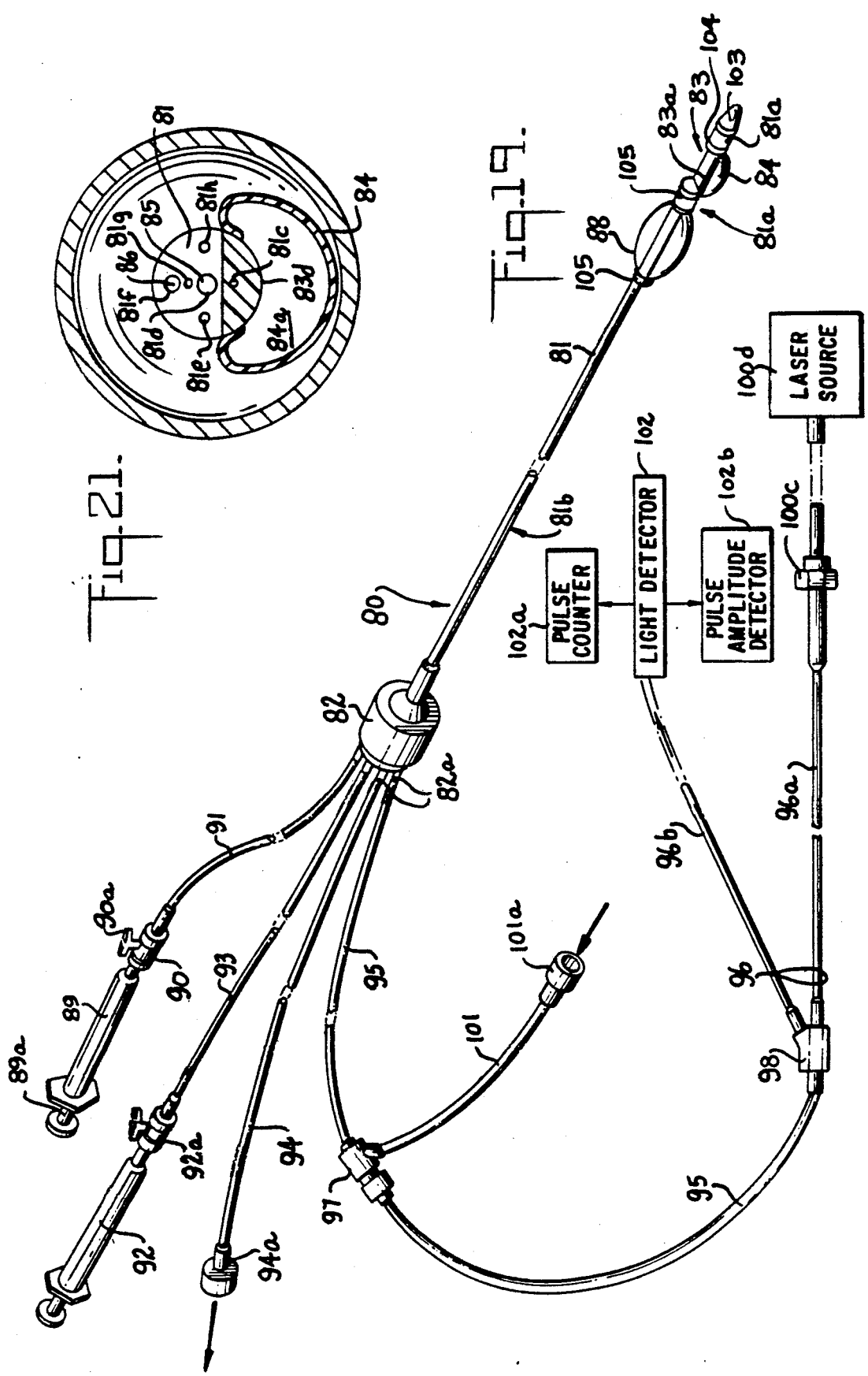

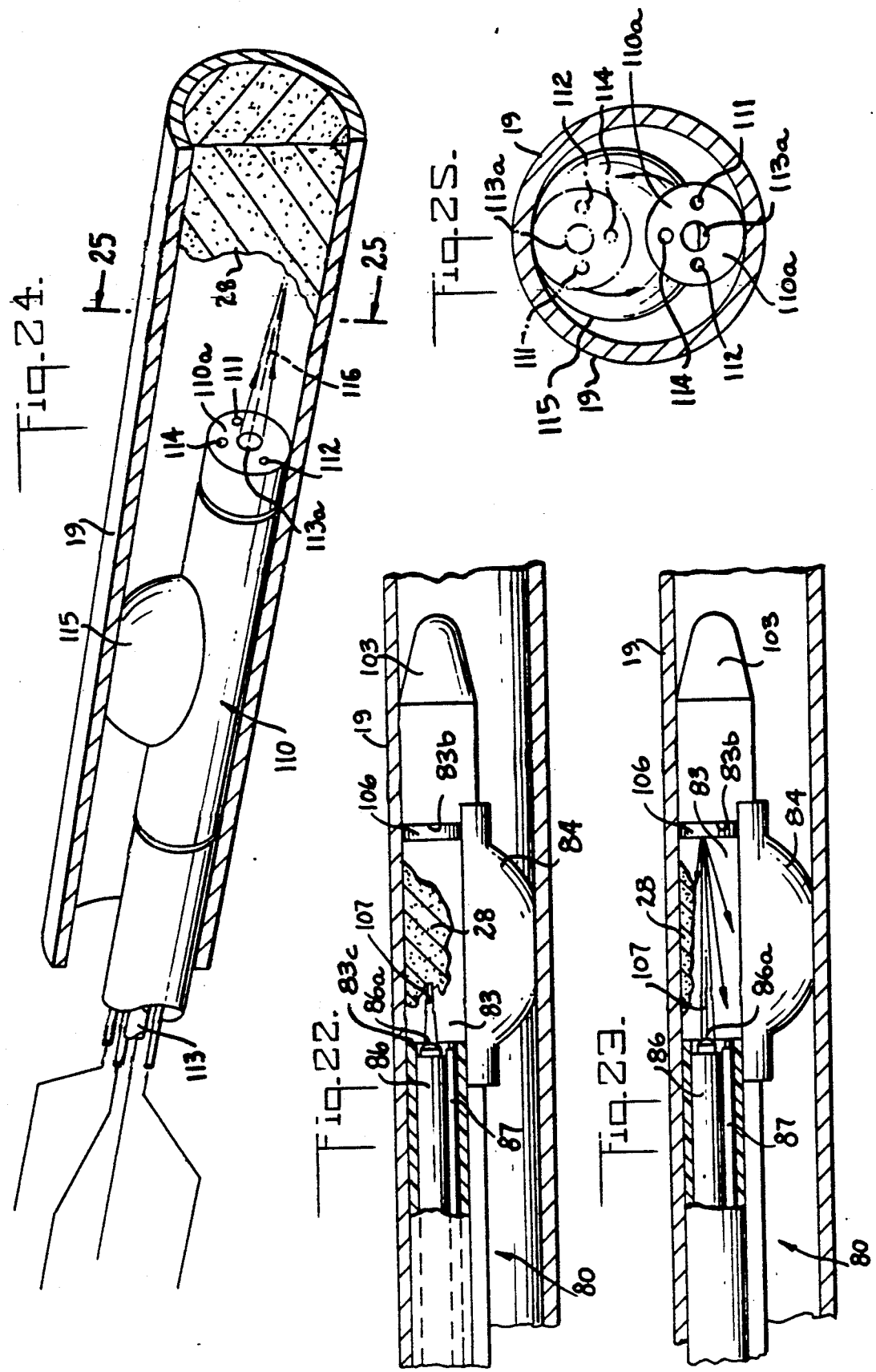

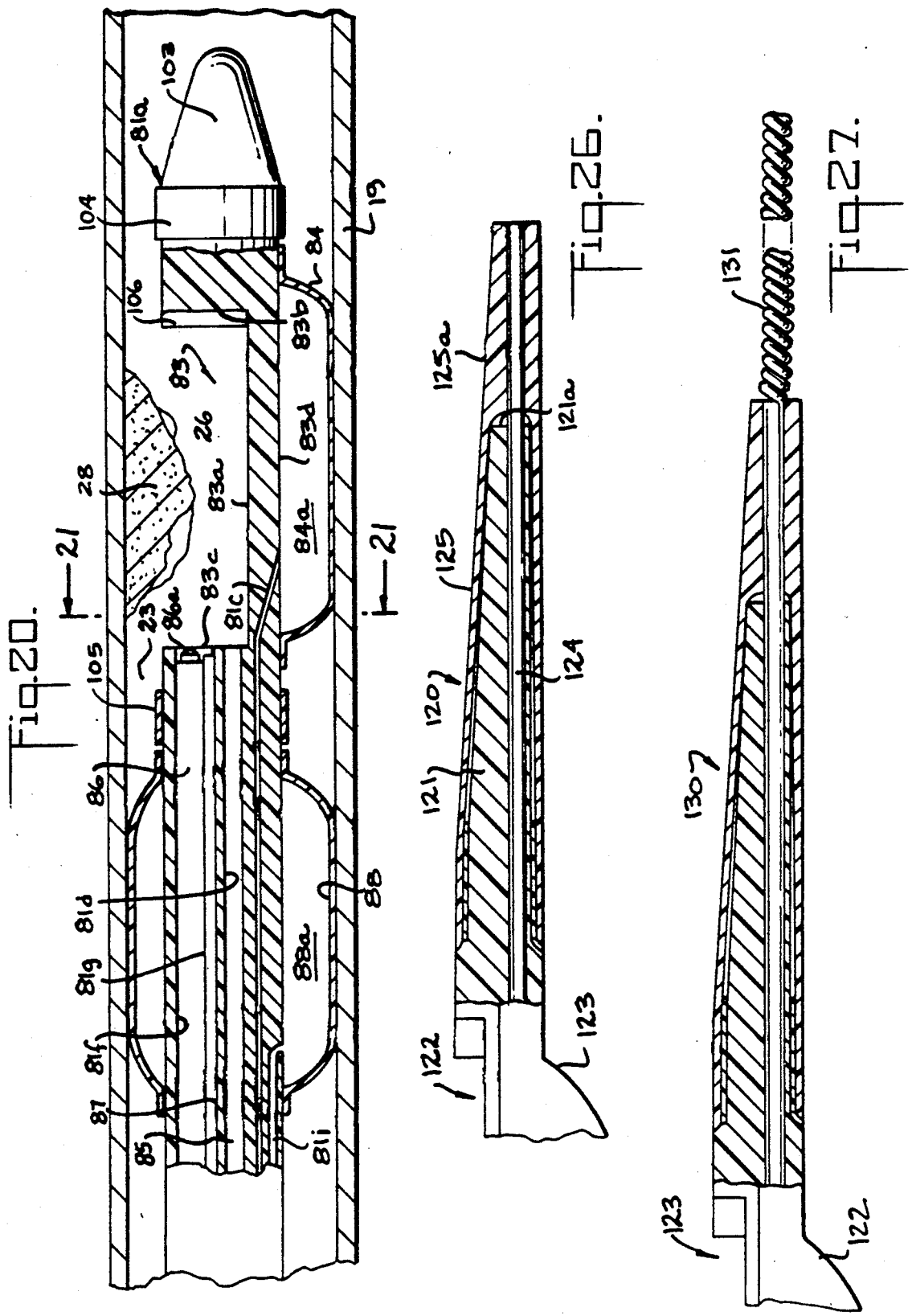

ANGIOPLASTY CATHETER AND METHOD OF USE THEREOF

This application is a continuation-in-part of application Ser. No. 585,112, filed Mar. 1, 1984, now U.S. Pat. No. 4,627,436.

BACKGROUND OF THE INVENTION

1. Field of the Invention

The invention relates to catheters which are adapted to be inserted in ducts and passages within the body as well as blood vessels including arteries and veins for the removal of blockages, obstructions, occlusions, or the like therefrom. More in particular, the invention relates to laser angioplasty, the use of laser energy to disintegrate or to vaporize plaque in coronary, femoral and other arteries. Laser angioplasty comprises the directing of a catheter which is adapted to transmit laser energy, into a blood vessel and the advancing of the free end of the catheter within the blood vessel to the location of an occlusion or arteriosclerotic plaque within the blood vessel. The catheter delivers laser energy to the location to disintegrate or vaporize the occlusion, thereby opening an obstructed blood vessel.

The use of the intense and concentrated energy of a laser within a portion of the body such as a blood vessel presents the possibility of perforation of the blood vessel and damage to the surrounding tissue. Accordingly, a catheter using laser energy must confine such energy to the obstruction to be removed.

2. Description of the Prior Art

Conventional catheters for laser angioplasty have a flexible outer tube which can be inserted into a blood vessel. Within the outer tube is disposed a bundle of optical fibers which extend to adjacent the distal end of the outer tube. A laser is connected to the bundle for transmitting laser energy to an occlusion within the blood vessel. Debris resulting from the vaporizing of the occlusion by the laser can be removed by applying suction to the outer tube.

U.S. Pat. No. 4,207,874 which issued to Choy on June 17, 1980 for a "Laser Tunneling Device" is an example of a catheter having a bundle of optical fibers. The catheter is adapted to be advanced within a blood vessel to adjacent an occlusion or calcified plaque for the application thereto of the energy of a laser. Suction can be applied to the laser to remove the debris resulting from the vaporization of the occlusion.

U.S. Pat. No. 4,224,929 which issued on Sept. 30, 1980 to Furihata for "Endoscope with Expansible Cuff Member and Operation Suction" discloses an endoscope adapted to be placed in a blood vessel. A pair of cuff members spaced apart from one another and disposed adjacent the distal end of the endoscope is adapted to be expanded to contact the inner walls of the blood vessel and to form a chamber between the cuff members. A procedure such as observation, surgical treatment, etc. can then be performed within the chamber formed by the cuff members and the blood vessel.

U.S. Pat. No. 4,240,431 which issued on Dec. 23, 1980 to Komiya for "Laser Knife" discloses a device using laser energy for the incision or excision of an affected part of the body. In order to prevent the laser energy from causing undesirable cautery or piercing of normal tissue adjacent that which is to be treated, the laser energy is intercepted by a receiving surface, once the cutting procedure is completed.

Russian Patent No. 938,977 which issued on Mar. 12, 1980 to Zaitsev discloses a device for dissecting the walls of blood vessels. The device utilizes a balloon which presses on a wall of the aorta thereby bending away a scalpel which enters through a window to make incisions in the aorta's central casing.

U.S. Pat. No. 4,445,892 which issued on May 1, 1984 to Hussein et al. discloses a dual balloon catheter device provided with two spaced expandable balloons for occluding a segment of a blood vessel. The patent also provides means for emitting laser irradiation.

International Patent Application No. PCT/US82/01669 of Garrett which published on June 9, 1983 discloses a catheter assembly including a first catheter and a second catheter positionable within the first catheter. An inflatable balloon is fixed to the outer surface of either the first or second catheter. When inflated, the balloon sealingly engages the interior of a body duct. The Garrett patent also discloses the use of a laser beam in order to remove an obstruction in a blood vessel.

U.S. Pat. No. 4,040,413 which issued on Aug. 9, 1977 to Ohshiro discloses one or more inflatable balloons on the outer surface of the tube of an endoscope which encloses a fiber optic light transmitting bundle.

SUMMARY OF THE INVENTION

The invention of a catheter device for use in removing undesired material from a duct within a patient's body comprises a catheter adapted to be disposed within a duct, means disposed adjacent to the distal end portion of the catheter for intersecting and releasing undesired material from the duct such as an occlusion or an accumulation of plaque within a blood vessel, and an inflatable bladder for positioning the distal end portion of the catheter adjacent the inner surface of the duct.

In one embodiment of the invention, a fiber optic within the catheter transmits laser energy to the distal end portion of the catheter for application to the undesired material.

In another embodiment of the invention, the distal end portion of the catheter including a pair of abutments which can form a chamber adjacent the inner surface of the blood vessel and prevent the escape of laser energy upon being applied to the undesired material.

In still another embodiment, the catheter is provided with a standoff to deflect the distal end portion of the catheter and thereby direct the laser energy away from the wall of the blood vessel.

In a further embodiment of the invention, the catheter includes an elongated element extending between abutments adjacent the distal end of the catheter for severing an occlusion or accumulation of plaque.

In still a further embodiment, the catheter includes a reflective or fluorescent layer at its distal end for returning light along a second fiber optic when the undesired material has been removed.

In yet another embodiment, the catheter includes two lumens, one adapted to contain, rotate around, and translate along a filament, e.g., a guidewire, and the other containing a fiber optic which can be rotated around the guidewire to bore through undesired material which almost completely blocks a blood vessel.

In still another embodiment of the invention, a catheter is provided which can notch a hole in a totally occluded stenosis without damaging the blood vessel in order that the catheters of the other embodiments of the invention may remove the remaining undesired material.

In yet another embodiment of the invention, a catheter is provided having an occluding balloon which impedes the flow of blood with respect to the catheter in order to provide a relatively blood-free environment in which the catheter may function.

In yet another embodiment of the invention, a catheter is provided having one or more radio-opaque bands to guide the catheter to adjacent an occlusion.

In still another embodiment of the invention, a catheter is provided having a soft, conically shaped nose to prevent or minimize damage to the blood vessel.

In yet another embodiment of the invention, a catheter is provided having an integral spring wire tip to direct the catheter through the blood vessel.

In yet another embodiment of the invention, a catheter is provided having a conically shaped distal end portion having at least one elongated opening therein to prevent or minimize clogging.

Therefore, it is an object of the invention to position the distal end of a catheter within a duct in a patient's body by remote control prior to the application of laser energy by the catheter.

It is another object of the invention to prevent the application of laser energy to the inner surface of the blood vessel as the laser energy is being applied to the plaque.

It is an additional object of the invention to rotate the catheter device within a blood vessel to apply laser energy to all portions of the interior of the blood vessel adjacent the distal end of the catheter.

BRIEF DESCRIPTION OF THE DRAWINGS

FIG. 1 is a perspective view of the laser angioplasty catheter of the invention showing a pair of abutments, a suction port therebetween, and an inflatable bladder;

FIG. 2 is a fragmentary vertical section of the catheter of FIG. 1 when disposed in a blood vessel adjacent to an accumulation of plaque therein;

FIG. 3 is a fragmentary vertical section of the catheter of FIG. 1 showing the abutments disposed adjacent to the plaque in the blood vessel and showing the bladder inflated;

FIG. 4 is a fragmentary vertical section of the catheter of FIG. 1 showing the application of laser energy to the plaque and the removal of the debris of the plaque by a vacuum lumen;

FIG. 5 is a transverse vertical section taken along the line 5—5 in FIG. 3 and showing the catheter positioned by the inflated bladder within a blood vessel;

FIG. 6 is a transverse vertical section of the catheter of FIG. 1 showing the catheter being rotated within a blood vessel;

FIG. 15 is a fragmentary perspective view of an embodiment of the catheter of the invention for use in boring a passage through an accumulation of undesired material in a blood vessel;

FIG. 16 is a fragmentary perspective view of the catheter of FIG. 15 showing a filament therein extended into a passage which has been bored through an accumulation of undesired material in a blood vessel;

FIG. 17 is a fragmentary perspective view of the catheter of FIG. 15 showing the catheter in positions resulting from rotating the catheter about the filament and showing the application of laser energy for boring out the accumulation;

FIG. 18 is a vertical section taken along the line 4—4 in FIG. 15 and showing the lumens of the catheter of FIG. 15 for each of a fiber optic for transmitting laser energy and the filament;

FIG. 19 is a perspective view of another embodiment of the laser angioplasty catheter of the invention showing an impedence balloon for impeding the flow of blood in a blood vessel when the catheter is disposed therein and a soft nose at the distal end of the catheter for preventing damage to a blood vessel in which the catheter is advanced;

FIG. 20 is a vertical section of the distal end portion of the catheter of FIG. 19 taken along the longitudinal axis thereof and showing laser energy being emitted across a chamber formed between two abutments of the catheter;

FIG. 21 is a transverse vertical section of the catheter of FIG. 19 taken along the line 21—21 in FIG. 20;

FIG. 22 is a fragmentary vertical section of the distal end portion of the catheter of FIG. 19 showing laser energy being applied to an accumulation in a blood vessel;

FIG. 23 is a fragmentary vertical section of the distal end portion of the catheter of FIG. 19 showing laser energy being reflected from a distal abutment toward an optical receiving fiber disposed in a proximal abutment as an obstruction within a blood vessel is being removed;

FIG. 24 is a fragmentary perspective view of another embodiment of the laser angioplasty catheter of the invention showing the emission of laser energy toward an obstruction which occludes a blood vessel;

FIG. 25 is a vertical section taken along the line 25—25 in FIG. 24 and showing the distal tip portion of the catheter of the invention with its positioning balloon and showing the pattern of the rotational movement of the catheter in a blood vessel;

FIG. 26 is a fragmentary vertical section of another embodiment of the catheter of the invention showing a FIG. 27 is a fragmentary vertical section of another embodiment of the distal end portion of the catheter of FIG. 26 having a helically coiled guidewire;

DESCRIPTION OF THE PREFERRED EMBODIMENTS

Figure 7:
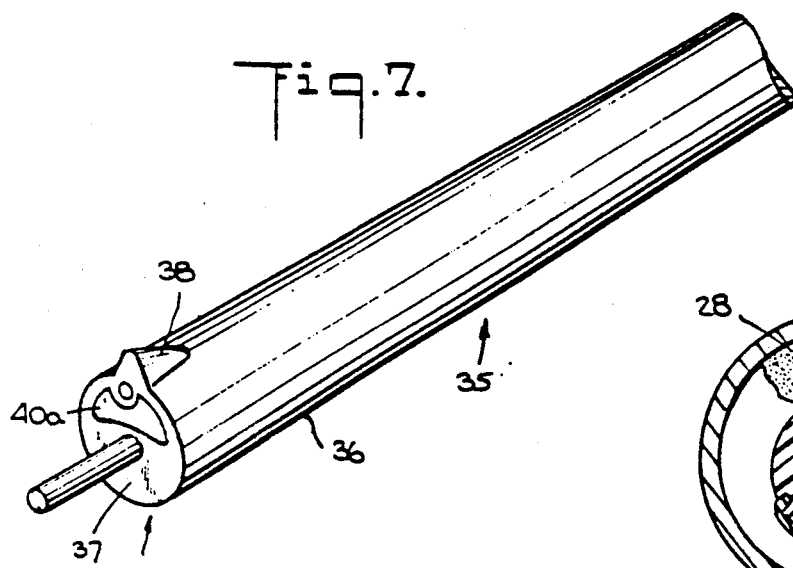
FIG. 7 is a fragmentary perspective view of another embodiment of the laser angioplasty catheter of the invention showing a standoff adjacent the distal end of the catheter for positioning the catheter within a blood vessel.

In FIG. 1 there is shown an embodiment of the catheter device of the invention comprising a laser angioplasty catheter device 20. Catheter device 20 includes catheter 21 having a distal end portion 21a and a proximal end portion (not shown). The diameter of the catheter is such that it can be readily introduced into and advanced along a blood vessel 19 of a patient, for example a coronary or a femoral artery. Thus the distal end portion of the catheter device is advanced along a blood vessel to the vicinity of an occlusion or an accumulation of plaque, either of which are to be removed from the blood vessel. The proximal end portion of the catheter remains external to the patient during the use of the catheter in destroying an occlusion or other lesions within a blood vessel. A pair of abutments 22 and 23 are disposed on the outer surface of catheter 21 adjacent distal end portion 21a of the catheter. The space between the abutments is adapted to form a working chamber when the catheter is positioned within a blood vessel adjacent to material such as an occlusion.

As shown in FIG. 2, catheter device 20 is provided with a filament or lumen 24 for positioning the catheter device within a blood vessel as will be described below. Filament 24 which extends along the interior of catheter 21 is free of the catheter in order that the catheter can be translated and rotated with respect to the filament. The filament can guide the catheter to the location of an occlusion by first advancing the distal end portion 24a of the filament to adjacent the obstruction to be treated. Thereafter, the catheter can be advanced along the filament until the distal end portion 21a of the catheter is adjacent to the obstruction. Since the filament within the catheter is free of the catheter, the catheter can be rotated with respect to the filament as the catheter is rotated within the blood vessel.

Further as shown in FIG. 2, there is provided fiber optic 25 having a proximal end (not shown) adapted to be connected to a source of laser energy and having a distal end portion 25a disposed within abutment 23. Typically the fiber optic can be a bundle of glass fibers or a single fiber adapted to transmit light including laser energy. By way of example, the source of laser energy may comprise a blue-green argon laser in the power range extending up to approximately twenty watts Laser energy emitted from the distal end portion 25a of the fiber optic is directed across chamber 26 formed between abutments 22 and 23 so that the laser energy can be intercepted and absorbed by abutment 22. In this way, the heating effect resulting from the application of laser energy is confined to chamber 26 and prevented from advancing along or into the blood vessel 25 by abutment 22.

In order to focus the laser energy into chamber 26, there may be provided refracting device or lens 27 mounted in abutment 23 at the distal end portion 25a of the fiber optic. The lens focuses and concentrates the laser energy into chamber 26 and insures that energy crossing the chamber is intercepted by abutment 22.

In FIG. 2, catheter device 20 is shown being advanced in the direction of the arrow toward plaque 28 attached to the inner surface 19a of blood vessel 19. The distal end portion 21a of the catheter is provided with bladder 29 which is shown in its relaxed position in FIG. 2. The distal end of lumen 30 extending within catheter 21 has an opening adjacent the inner surface of bladder 29. The proximal end of lumen 30 (not shown) can be connected to a suitable source of fluid pressure such as air pressure of a level which is adapted to inflate bladder 29 into the positions shown in FIG. 3.

Also shown in FIG. 2 is suction port 31, disposed between abutments 22 and 23. Lumen 32 has its distal end portion 32a in communication with suction port 32. The proximal end of lumen 32 (not shown) can be connected to a suitable source of pressure which is less than the ambient pressure such as a vacuum source. Accordingly, suction port 31 is adapted to receive flow from within the blood vessel and to enable such flow from within the blood vessel and to enable such flow to be transmitted by means of lumen 32.

In FIG. 3, the catheter device 20 is shown positioned within blood vessel 19 with abutments 22 and 23 positioned at the opposite sides of plaque 28 which is to be removed from the inner surface 19a of the blood vessel. The inflation of bladder 29 causes the bladder to contact the inner surface of the blood vessel and urge distal end 21a of the catheter toward the inner surface of the blood vessel opposite the inflated bladder with the result that the abutments 22 and 23 bear against the inner surface of the blood vessel at the opposite sides of the plaque 28. In this way, the plaque is substantially trapped within chamber 26 formed by the abutments.

Laser energy is then applied to fiber optic 25 and emitted at the distal end 25a of the fiber optic into chamber 26 where the laser energy encounters the plaque 28. The laser energy is adapted to heat the plaque and lead to its disintegration as the plaque tends to vaporize in response to the heating. As the plaque disintegrates, abutments 22 prevents the release of laser energy into the blood vessel in advance of the end portion of the distal end 21a of the catheter. The laser can be pulsed or can be switched in a manner to control the intensity and level of the energy being delivered to the plaque. During the application of laser energy, bladder 29 is maintained in an inflated state in order to keep the abutments against the inner surface of the blood vessel.

In FIG. 4, laser beam 33 shown by a dotted line extends across chamber 26 as the plaque is being vaporized. The laser beam after crossing the chamber is intercepted by abutment 22 which can absorb the remaining level of energy and prevent it from being transmitted within the blood vessel. The debris as shown in FIG. 4 flows in the direction of the arrows through the port and into lumen 32 in response to reduced pressure or vacuum therein, thereby removing the debris from the site of the plaque at the inner surface of the blood vessel.

In FIG. 5, the catheter device is shown positioned within blood vessel 19 with bladder 29 inflated and with plaque 28 displaced to one side of the chamber 31 formed between the abutments.

In FIG. 6, the catheter device 20 is shown being rotated in the direction of the arrow in order to position plaque 28 within chamber 31. The rotational movement of the device is caused by the application of rotational movement or torque to catheter 21. Accordingly, the catheter device can be rotated about filament 24 to sweep the complete interior of the blood vessel circumferentially and insure removal of all plaque or the like therein.

Figure 8:
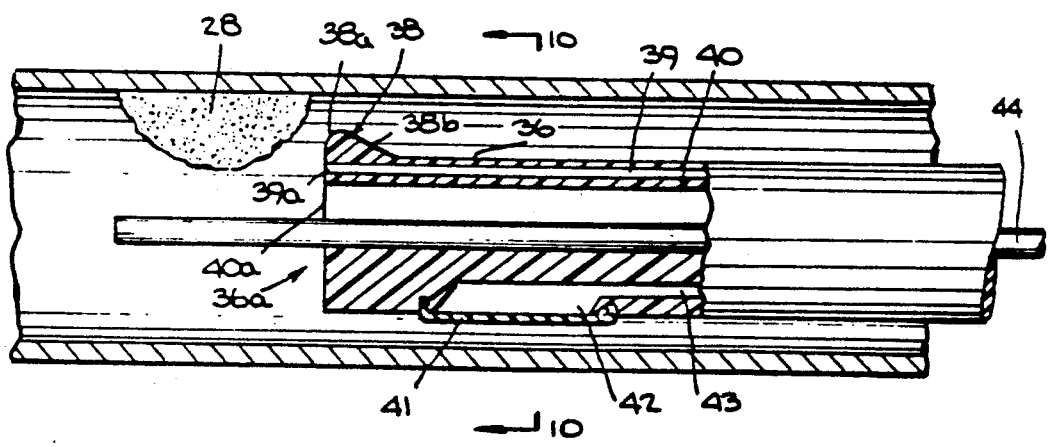
FIG. 8 is a fragmentary vertical section showing the catheter of FIG. 7 being positioned adjacent to plaque within a blood vessel.

In FIG. 7, there is shown another embodiment of the laser angioplasty catheter 35 of the invention. Catheter device 35 comprises catheter 36 having a distal end portion 36a partially closed by wall 37. As shown in FIG. 8, the outer surface of catheter 36 adjacent the distal end portion 36a thereof is provided with standoff 38 having an apex 38a and a ramp 38b. The catheter has fiber optic 39 disposed therein. The fiber optic has a distal end portion 39a which is adapted to release laser energy into a blood vessel when the proximal end portion (not shown) of fiber optic 39 is connected to a source of laser energy external to the patient. The catheter device 35 also includes lumen 40 disposed within catheter 36 and having distal end portion 40a. The distal end portion of the lumen can be in the form of a crescent-shape as shown in FIG. 7.

Figure 9:
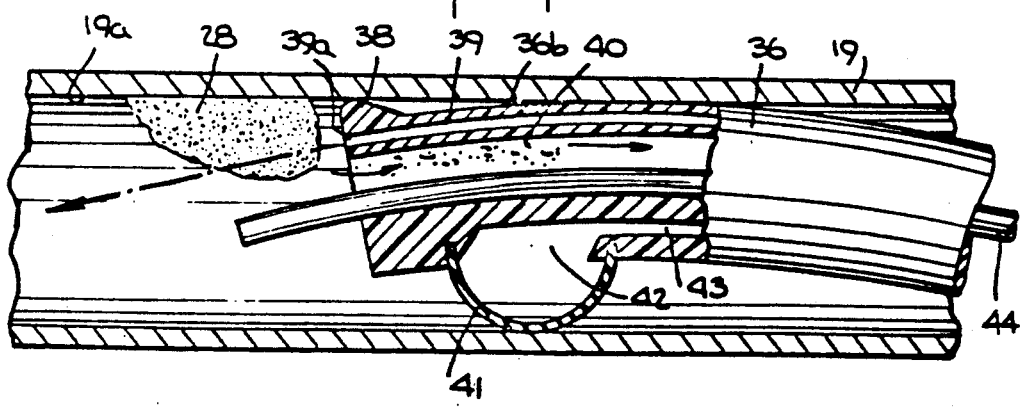
FIG. 9 is a fragmentary vertical section of the catheter of FIG. 7 showing the standoff urged against the inner surface of a blood vessel in response to the inflation of the bladder.

Catheter device 35 also includes bladder 41 disposed adjacent the distal end portion 36a of the catheter and substantially opposite standoff 38. The bladder overlies port 42 to which is connected lumen 43. Lumen 43 when its proximal end portion (not shown) is connected to a fluid pressure source is adapted to inflate the bladder as shown in FIG. 9. Inflation of the bladder urges standoff 38 against the inner surface 19a of the blood vessel and the outer surface of the catheter 36 adjacent to the standoff 38. As a result, the distal end portion 36a of the catheter assumes the curved form shown in FIG. 9 with the result that the distal end 39a of the fiber optic is directed toward the center line of the blood vessel. In this position as shown in FIG. 9, the laser energy can be directed against plaque 28. With the application of negative pressure or vacuum to lumen 40, debris from the plaque enters the crescent-shaped opening 40a of the lumen and thereby is removed from the blood vessel.

Figure 10:
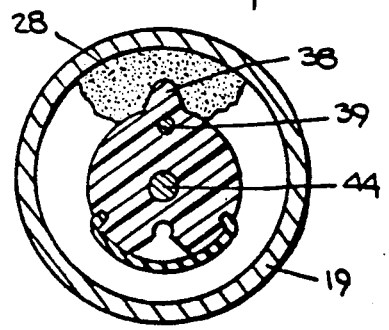
FIG. 10 is a transverse vertical section taken along the line 10—10 in FIG. 8 and showing the catheter of FIG. 7 disposed within a blood vessel prior to inflation of the bladder.

As shown in FIG. 10, catheter 35 can be rotated about filament 44 in order to bring the laser energy emitted from fiber optic 39 substantially into alignment with plaque 28. In addition, the filament enables the catheter device 35 to be rotated throughout the inner circumference of the blood vessel in order to sweep the entire interior of the blood vessel with the laser energy.

Figure 11:
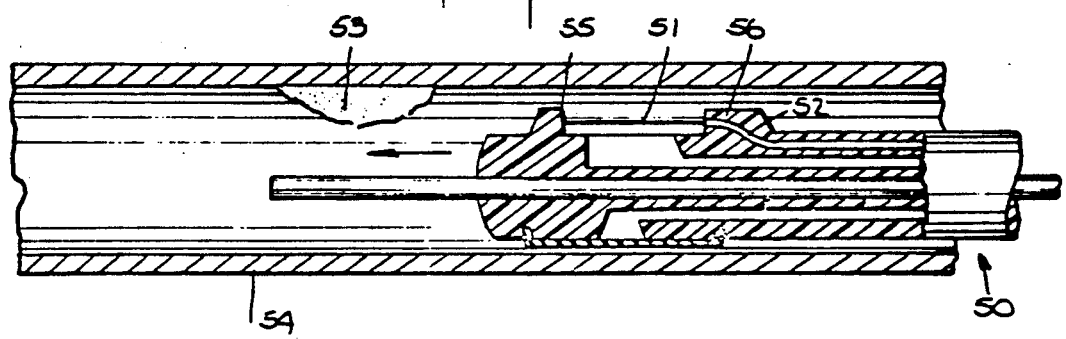
FIG. 11 is a fragmentary vertical section of another embodiment of the catheter of the invention which includes a heated element for releasing undesired material from a blood vessel.
Figure 13:
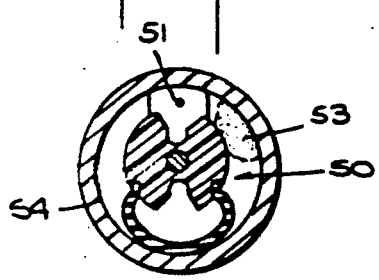
FIG. 13 is a vertical section showing the catheter of FIG. 12 positioned by the inflated bladder within a duct.

In FIG. 11, there is shown an embodiment of the catheter device 50 of the invention in which the means for intersecting and releasing undesired material from the interior of a duct of a patient, such as a biliary duct, a duct associated with the gall bladder, etc. Catheter device 50 includes heating element 51 which can comprise resistance wire such as that of Nichrome wire. Leads 52 are adapted to deliver electrical energy to the heating element 51. Rotation of catheter 50 as shown in FIG. 13 enables the heating element to intersect and release undesired material 53 from the inner surface of duct 54.

Figure 12:
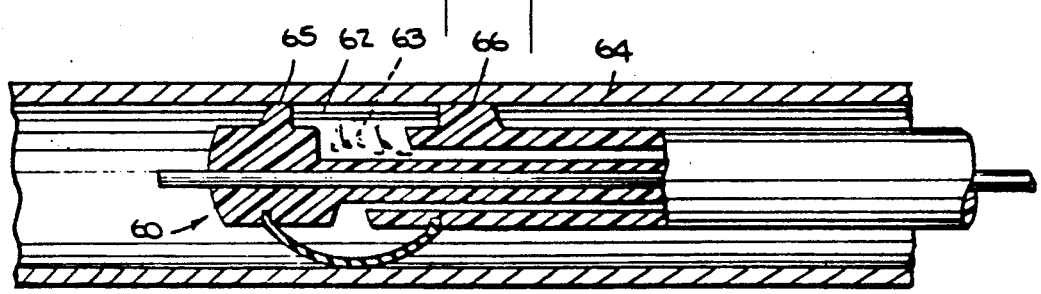
FIG. 12 is a fragmentary vertical section of still another embodiment of the catheter of the invention which includes a blade for releasing undesired material from a blood vessel.
Figure 14:
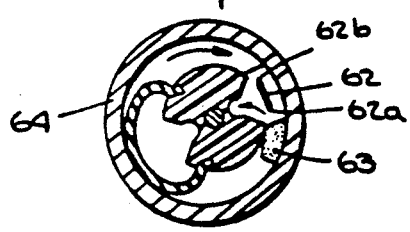
FIG. 14 is a transverse vertical section view of the catheter of FIG. 13 showing the catheter of FIG. 12 being rotated within a blood vessel.

In FIG. 12, there is shown an embodiment of the catheter device 60 of the invention in which there is provided a blade 62 for intersecting and releasing undesired material 63 from the inner surface of duct 64. Blade 62 as shown in FIG. 14 includes oppositely disposed edges 62a and 62b which are adapted to sever undesired material 63 as catheter device 60 is rotated within duct 64.

In FIGS. 15-18 there is shown another embodiment of the catheter device of the invention. Catheter device 70 comprises a housing 71 having a figure-8 or "double barrel" form with a first lumen 72 and a second lumen 73. The first lumen 72 is adapted to receive the length of a filament or guidewire 74 in order that housing 71 may be translated along and rotated about the filament 74 (FIGS. 15-17). The second lumen 73 is adapted to receive an optical fiber 75. Preferably, the lumens 72 and 73 are of a predetermined bore size which enable a filament 74, e.g., a guidewire, to be readily passed through the first lumen 72 and optical fiber 75 to be passed through the second lumen 73. Preferably, the distal end portion 75a of the optical fiber 75 is positioned flush with the distal end 73a of the second lumen 73. The diameter of the housing 71 is such that it can be conveniently introduced into and advanced along a blood vessel 19 of a patient, for example, a coronary or femoral artery. An X-ray fluoroscopic device can be used to observe the movement of the catheter within the blood vessel. Thus, the distal end 71a portion of the housing 71 is advanced along a blood vessel to the vicinity of an occlusion or an accumulation of plaque 28.

FIG. 16 shows the catheter device 70 of FIG. 15 in a blood vessel or duct which is almost completely blocked, e.g., up to about 99% stenosis. Thus undesired material 28 is adhering to the inner surface of the blood vessel 19 and there is virtually no room to pass a catheter device. The filament 74 upon being advanced with respect to the first lumen 72 emerges at the distal end 71a of the housing 71 and is extended into the undesired material 28. The filament 74 has a sufficient diameter to enable it to pass through the passage 28a extending through the undesired material 28. If the blood vessel is not totally occluded, there will normally be such a path or passage 28a extending through the undesired material 28.

Once the filament 74 has been passed through the passage 28a in the undesired material, the end portion 71a of the housing 71 can be moved along the axis of the filament 74 to adjacent the undesired material 28. The second lumen 73 is adapted to contain a fiber optic 75 which is connected at its proximal end to a source laser energy (not shown). The laser energy is released at the distal end portion 75a of the fiber optic 75 in the direction of undesired material 28. Preferably, the distal end portion 75a of the fiber optic 75 has a polished convex surface which focuses the laser energy toward the undesired material at a short distance therefrom. In this way, the laser energy is concentrated on the accumulation 28 to increase the ability of the laser energy to disintegrate the accumulation.

In FIG. 17, the distal end of housing 71 is shown positioned adjacent to the undesired material 28 within blood vessel 19. Laser energy 76 can then be transmitted through fiber optic 75. The end portion 71a of the housing 71 is translated to adjacent the accumulation 28 along filament 74 and then rotated about the filament 74 to cause the fiber optic 75 to revolve about filament 74 and progressively ablate or vaporize amounts of undesired material. The rotation is shown by dot-dash lines in FIG. 17.

In FIG. 19, there is shown another embodiment of the laser angioplasty catheter system or device of the invention. Catheter device 80 comprises catheter 81 having a distal end portion 81a and a proximal end portion 81b. The diameter of the catheter 81 is such that it can be readily introduced into and advanced along a duct or blood vessel 19 of a patient, for example, a coronary or a femoral artery. Again the movement of the catheter within the artery can be observed and controlled bY use of X-ray fluoroscopic equipment. The distal end portion 81a of the catheter is advanced along a blood vessel to adjacent an occlusion or an accumulation of plaque, either of which are to be removed from the blood vessel. The proximal end portion 81b of the catheter remains external to the patient during use of the catheter. Connected to the proximal end portion 81b by proximal connector 82 are a number of tubes 91, 93, 94 and 95 for the passage of fluids, gases, solids and laser energy to a plurality of lumens of the catheter.

As shown in FIGS. 19, 20 and 21, the distal end portion 81a of catheter 81 includes open chamber 83 formed by bottom wall 83a and abutments 83b and 83c. Positioning balloon 84 is attached to the outer surface 83d of bottom wall 83a. As shown in FIG. 21, abutment 83c is intersected by lumens 81c, 81d, 81e, 81f, 81g, and 81h.

Lumen 81c which communicates with the interior 84a of balloon 84 is adapted to inflate and deflate the balloon in response to the pressure condition of fluid such as air in lumen 81c.

Lumen 81d is adapted to receive a guidewire 85 in slidable engagement therewith. The guidewire can be used to position the chamber 83 adjacent an occlusion 28 as shown in FIG. 20. If guidewire 85 is removed from lumen 81d, the lumen 81d then becomes available for other uses such as a passage for aspirating undesired material 28 from chamber 83.

Lumen 81e is available to serve as a passage in communication with chamber 83. For example, lumen 81e can be used to deliver a liquid to chamber 83 for irrigating the chamber and the portion of the interior of the blood vessel 19 adjacent thereto.

Lumen 81f is adapted to receive a fiber optic 86 with the distal end portion 86a of the fiber optic being exposed in abutment 83c. Fiber optic 86 is adapted to transmit laser energy into chamber 83 and against undesired material 28 therein in order to disintegrate such material for subsequent removal.

Lumen 81g is adapted to receive fiber optic 87 which can transmit reflected light from chamber 83 as disclosed subsequently herein.

Lumen 81h is an alternate fluid passage in communication with chamber 83.

As shown in FIGS. 19 and 20, catheter device 80 includes occlusion balloon 88 surrounding catheter 81 adjacent chamber 83. The interior 88a of balloon 88 is in communication with lumen 81i in catheter 81 which is adapted to apply controlled fluid pressure to the interior 88a of balloon 88. When inflated by fluid pressure, the periphery of balloon 88 abuts the inner wall of blood vessel 19 and serves to cut off the flow of blood within the blood vessel. For example, when inflated, balloon 88 can prevent the movement of blood from the left as viewed in FIG. 20 and toward chamber 83. Thus, the chamber can be isolated from inflowing blood during use of the catheter device 80.

Within the interior of proximal connector 82, a plurality of passages are provided (not shown), each of which can be connected to a different one of lumens 81c–81i of catheter 81. A plurality of fittings 82a extending from proximal connector 82 are each connected to a different one of lumens 81c–81i.

A source of fluid pressure for inflating positioning balloon 84 comprises syringe 89. The syringe is connected by one-way stop cock 90 to tube 91. When plunger 89a of the syringe is operated, fluid pressure is transmitted through stop cock 90, tube 91, proximal connector 82, to lumen 81c which inflates positioning balloon 84. When the positioning balloon 84 is inflated, open chamber 83 is moved upwardly as viewed in FIG. 20, thereby causing accumulation 28 to be disposed in the chamber. The one-way stop cock 90 acts as a check valve to hold a level of pressure in tube 91 and lumen 81c after pumping by the operation of plunger 89a ceases. To release such pressure, the stop cock 90 is operated by handle 90a to vent the pressure, thereby enabling the positioning balloon 83 to collapse.

Syringe 92 which can be similar to syringe 89 is connected by one-way stop cock 92a, tube 93, proximal connector 82 and lumen 81i to occlusion balloon 84. The occlusion balloon when inflated by operation of syringe 92 fills the space between catheter 81 and the interior of the blood vessel as shown in FIG. 20. The result is that a flow of blood toward chamber 83 is occluded as well as a flow from the area of the chamber toward the occlusion balloon. In this way, blood can be blocked from the area of the chamber during the operation of the catheter device 80 to remove an accumulation of undesired material. The location of balloon 84 can be adjacent to chamber 83 as shown in FIG. 20 or can be positioned along catheter 81 at a predetermined distance from chamber 83.

In FIGS. 19 and 20, there is shown tube 94 connected through proximal connector 82 to lumen 81d of catheter 81. The end portion of tube 94 opposite the end thereof attached to connector 82 is provided with a male Luer fitting 94a which enables the tube to be connected to a source of negative pressure. Accordingly, lumen 81d can aspirate material from chamber 83. In the alternative, tube 94 can receive a guidewire 85 which is to be inserted into lumen 81d and extended to adjacent chamber 83. The guidewire can be used to advance catheter device 80 along a blood vessel when viewed by an X-ray fluoroscopic device until chamber 83 is disposed adjacent to an occlusion to be removed. The bores of both the tube 94 and the lumen 81d are dimensioned to enable catheter 81 to be translated and rotated with respect to the portion of the guidewire extending through tube 94 and lumen 81d.

In FIG. 19, there is additionally shown tube 95 which extends from proximal connector 82, through hemostasis valve assembly 97 to optical "Y" connector 98. Tube 95 has a bore which can receive a bundle 96 of fiber optic elements 96a and 96b. Elements 96a and 96b extend through the interior of tube 95 and hemostasis valve assembly 97 to proximal connector 82. The connector 82 couples fiber optic elements 96a and 96b to fiber optics 86 and 85, respectively, of catheter 81.

Connector 100c connects fiber optic 96a to a source of laser energy (not shown) which can transmit laser energy into chamber 83. The free end of fiber optic 96b can be connected to a light energy detection device 102 which can detect light returned from chamber 83 when the laser energy is applied to the chamber.

Tube 101 is connected to hemostasis valve 97 and thereby to the interior of tube 95 in which the bundle 96 of fiber optics 96a and 96b is disposed. A male Luer fitting 101a is connected to the free end of tube 101. Tube 95 is connected to a fitting 82a of proximal connector 82 which in turn is connected to lumen 81e of catheter 81. When fitting 101a is connected to a source of irrigating fluid such as saline, the irrigating fluid can be delivered by tube 101, tube 95, and lumen 81e to chamber 83. Valve 97 enables the supply of irrigating fluid from tube 101 to be controlled or shut off.

As shown in FIG. 20, at the distal end 81c of the catheter device 80 there is disposed a conically-shaped nose 103 of soft or compliant resin or elastomeric material which assists the catheter device in passing along a blood vessel and reduces the possibility of causing trauma to the blood vessel. The nose also assists the catheter device in entering one of a plurality of branches of a blood vessel at a junction therein. Thus, the soft nose can prevent possible damage to the blood vessel by passing smoothly into one of the branches of a junction of branches.

Radio-opaque bands 104 and 105 (FIGS. 19 and 20) substantially absorb or block X-ray radiation when an X-ray fluoroscope is used to guide the chamber 83 to adjacent an occlusion 28. Since the bands block X-ray radiation while the regions adjacent thereto transmit the radiation, the bands can be readily recognized when viewing the catheter or a fluoroscopic presentation, thereby showing the location of chamber 83 in the blood vessel. The radio-opaque bands 86 may be located adjacent abutments 83b and 83c.

Abutment 83b is formed of material which can absorb the laser energy radiated from distal end portion 86a of fiber optic 86 into chamber 83. The laser energy is thereby blocked from contacting the blood vessel adjacent to chamber 83. As shown in FIG. 20, a layer 106 of material can be mounted on abutment 83b. This layer of material can be reflective to laser energy, thereby directing a portion of the laser energy toward fiber optic 87. In turn, fiber optic 87 transmits the reflected laser energy to fiber optic 96b. A laser energy or light responsive sensor 102 is connected to fiber optic 96b in order to sense the presence of laser energy or light reflected from abutment 83b or layer 106 thereon. As the laser energy from fiber optic 86 penetrates and disintegrates occlusion 28 in chamber 83, an increasing portion of the laser energy will impinge on abutment 83b or layer 106 and then be reflected toward fiber optic 87. The light responsive sensor 102 connected to fiber optic 96b then detects the reflected laser energy. As the occlusion is progressively disintegrated by the laser energy, the level of reflected laser energy will increase until a maximum level is detected at the time when the laser energy is no longer intercepted by the occlusion. In this way, the operator of catheter device 80 can determine how the procedure of disintegrating the occlusion is progressing and when the procedure is completed.

Layer 106 can be formed of material which fluoresces when subjected to laser energy. Such fluorescent material multiplies the level of the light being reflected and thereby enhances detection of the reflected light transmitted by fiber optic 87. The phosphor material of the fluorescent material of layer 106 can be selected to give the color of light most readily detected under the operating conditions of chamber 83. In addition, the fluorescent layer by selection of the phosphor material enables the reflected fluorescent light to be at a predetermined wave length which is distinct for that of the laser energy, thereby enhancing detection of reflected light for chamber 83.

The source of laser energy 100d can, by way of example, comprises a source of pulsed laser energy. Further by way of example, the repetition rate can be five pulses per second. When the laser pulses enter the chamber 83 at the distal end of the catheter device 80, the fluorescent target 106 will respond to the laser pulses into the chamber even though the undesired material extends across the chamber. Accordingly, the fluorescent target will reflect or transmit pulses of light to fiber optic 87, fiber optic 95 and fiber optic 96b to light detector 102 which can include a photodetector such as silicon photodiode. The light pulses from the light detector 102 are counted by pulse counter 102a in order to ensure that the pulses of laser energy are actually being applied to the chamber 83. Thus, for example, the counter 102a can count pulses over a predetermined time period such as two seconds. Failure to count the proper number of pulses in the predetermined time period indicates that there is a fault in the system for delivering pulses of laser energy to the chamber 83.

The output of the light detector is also connected to pulse amplitude detector 102b in order to measure the amplitude of the pulses. The amplitude is of a minimum level when the chamber is substantially filled by the undesired material which blocks a major portion of the laser energy from reaching the fluorescent target 106. As the undesired material is disintegrated, an increasing portion of the laser energy portion strikes the target 106. When all of the undesired material is disintegrated and removed from the chamber, a maximum amplitude will be detected by the pulse amplitude detector 102b. In this way, the procedure for eliminating the undesired material from the chamber can be monitored and controlled.

Catheter device 80 is shown being urged upwardly as viewed in FIG. 20 against the inner surface of blood vessel 19 by inflation of positioning bladder 84. Occlusion balloon 88 is shown inflated. Catheter device 80 when in a blood vessel can be rotated about filament 85 in order to bring laser energy emitted from fiber optic 86 into contact with obstruction 28. The irrigation lumen 81e when connected by tubes 95 and 101 to a source of irrigating fluid can irrigate the chamber 83 and facilitate the break down of the obstruction 28. The irrigation fluid or solution, e.g., saline, can be removed through lumen 81d when guidewire 85 is removed therefrom.

In FIG. 22, catheter device 80 is shown with balloon 84 inflated, thereby urging abutments 83a and 83b against the inner surface of the blood vessel 19 with the obstruction 28 which is to be removed from the inner surface of the blood vessel disposed between the abutments. Laser energy 107 is shown being emitted from fiber optic 86 and contacting the obstruction 28 with the laser energy being confined to the chamber 83 by the abutments. In FIG. 23 the laser energy 107 is shown after substantial disintegration of the obstruction 28 which is removed from the chamber 83 by means of the aspiration lumen 81d. As obstruction 28 is progressively removed from the path of laser energy 107, the laser energy contacts the reflective layer 106 of abutment 83b which progressively reflects laser energy proximally toward the receiving fiber optic 87, thereby transmitting the reflected energy to the sensor 102.

FIG. 24 illustrates yet another embodiment of the laser angioplasty catheter of the invention, i.e., laser boring catheter 110. Catheter 110 has a relatively flat distal end 110a in which is disposed the open distal end portions of aspiration lumen 111 and irrigation lumen 112, the distal end portion of fiber optic 113, and plugged balloon lumen 114. A guidewire (not shown) may be inserted through aspiration lumen 111 for the purpose of directing translation of laser boring catheter device 110 with respect to the blood vessel 19. The plugged balloon lumen 114 communicates with the interior of positioning balloon 115 in order to inflate the balloon and urge the catheter against the wall of the blood vessel as shown in FIG. 24.

In practice, the laser boring catheter device 110 is guided by an X-ray monitor, e.g., fluoroscope, to a site in a blood vessel which is totally occluded by an obstruction 28. As the bladder 115 is inflated, the laser boring catheter 110 can be rotated about a guidewire (not shown) disposed in either of lumens 112 or 113 to position fiber optic 113 at a desired location within the blood vessel 19. There may be provided refracting device or lens 113a mounted at the distal end portion of the fiber optic 113 to converge the laser energy 114 on the obstruction 28 as the laser energy is emitted from the fiber optic. It is contemplated that the laser boring catheter device 110 can be used to "notch" a hole into a totally occluded stenosis in order that another catheter, e.g., one of the catheters disclosed herein, can be positioned adjacent to the remaining obstructing material 28 and effectuate its removal. Prior to and during the application of laser energy 114, an irrigation fluid, e.g., saline, is delivered through irrigation lumen 112 toward the obstruction, thereby filling the adjacent volume between the distal tip 110a of the laser boring catheter 110 and the obstruction. The volume is then aspirated through aspiration lumen 113.

In FIG. 25, the laser boring catheter device 110 is shown positioned within blood vessel 19. Laser boring catheter 110 is shown positioned against the inner wall of blood vessel 19 in response to the force produced by the inflation of balloon 115. As shown in FIG. 25, laser boring catheter 110 may be rotated adjacent the inner surface of blood vessel 19 in order to direct laser energy 114 to a circular pattern of different portions of obstruction 28.

FIG. 26 illustrates another embodiment of the laser boring catheter, i.e., catheter 120. Catheter 120 comprises a tapered end portion 121 extending beyond positioning balloon 122 and chamber 123. Guidewire lumen 124 extends through the tapered portion. Soft tubing material 125 covers the tapered portion and extends beyond at least the distal end 121a of the tapered portion, thereby substantially covering the laser boring catheter 120. The distal tip 125a of the soft tubing material 125 prevents damage to a blood vessel as the catheter 120 is advanced.

FIG. 27 illustrates laser boring catheter 130 having an integral springwire tip 131 for the purpose of directing catheter 130 through the blood vessel. The tip 131 is compliant and therefore the tip will readily advance into one of a plurality of blood vessels at a junction thereof. In this way, the tip can guide catheter 130 without damage to the blood vessels.

Figure 28:
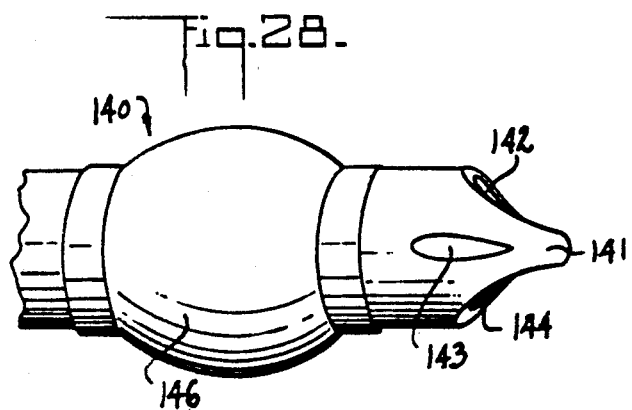
FIG. 28 is an elevation view of another embodiment of the distal end portion of the catheter of the invention showing elongated openings in the distal end portion thereof to prevent clogging thereof.
Figure 29:
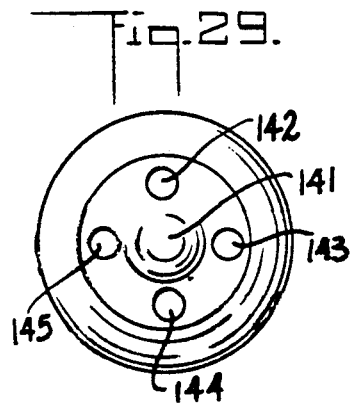
FIG. 29 is an end view of the distal end portion of the catheter of FIG. 28.

FIGS. 28 and 29 illustrates an alternate embodiment of the laser boring catheter 140 of the invention. The distal tip 141 of laser boring catheter 140 is conically-shaped with a decreasing radius and elongated openings 142, 143, 144, and 145. Opening 142 leads to the fiber optic. Opening 145 leads to the irrigation lumen. Opening 144 leads to the aspiration guidewire lumen. Opening 143 which leads to the inflating lumen for balloon 146 is plugged. The elongated openings of this embodiment of the laser boring catheter serve to prevent the openings from being damaged or clogged by blood or debris from the obstruction to be disintegrated by laser energy. Preferably, conically-shaped distal tip 141 is made of a soft resin or elastomeric material to prevent damage to the blood vessels.

Figure 30:
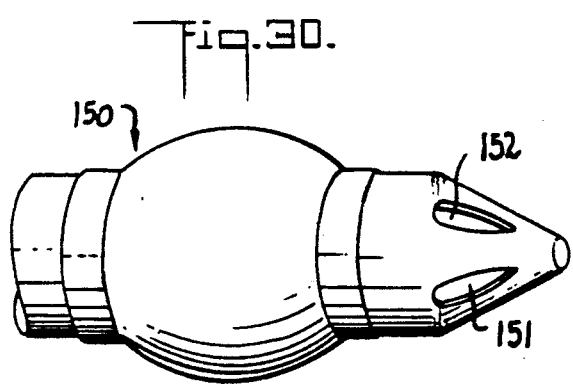
FIG. 30 is an elevation view of the distal end portion of another embodiment of the catheter of the invention showing an opening in the center thereof for transmitting laser energy.
Figure 31:
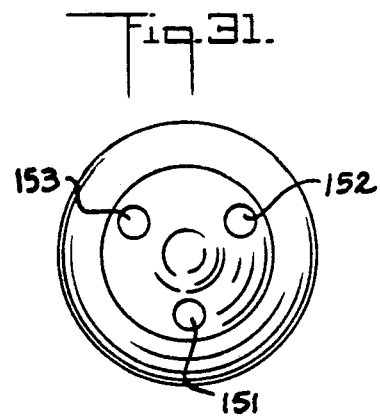
FIG. 31 is an end view of the distal end portion of the catheter of FIG. 30.

FIGS. 30 and 31 shows laser boring catheter 150 which is similar to catheter 140. Opening 151 is connected to the guidewire lumen. Opening 152 is connected to the lumen for irrigating fluid. Opening 153 which is plugged is connected to a lumen (not shown) for inflating the occlusion balloon 154. Opening 155 is connected to a lumen (not shown) for receiving the laser optical fiber.

Figure 32:
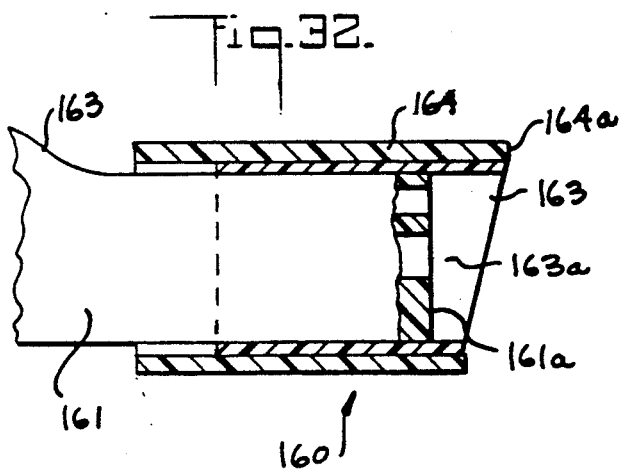
FIG. 32 is a vertical section view of a collar and sheath for the distal end portion of the catheter of FIG. 24.

In FIG. 32, there is shown laser boring catheter device 160 having catheter 161 with a distal end portion 161a. Lumen 161b contains fiber optic 162 which terminates at the distal end portion 161a. Irrigating lumen 161c similarly terminates at the distal end portion 161a. Lumen 161d which is plugged adjacent distal end portion 161a is adapted to deliver pressured fluid for inflating positioning balloon 163. Lumen 161c which terminates at distal end portion 161a is adapted to aspirate the region of a blood vessel adjacent thereto.

In order to prevent contact of the distal end portion 161a with an obstruction or accumulation in a blood vessel, a cylindrical collar 163 is placed about catheter 161, extending from the distal end portion thereof toward positioning balloon 163. Accordingly, an open chamber 163a is formed by the collar 163 in advance of the distal end portion 161a. The collar 163 can be formed of rigid material such as metal or resin material. In order to prevent the possibility of the rigid collar 163 injuring or damaging the inner surface of a blood vessel during operation of the catheter, a protective sheath 164 which is formed from soft resin or elastomeric material is extended over collar 163 and the portion of catheter 161 adjacent the distal end portion thereof. Since the end portion 164a of the sheath extends beyond the end portion 163a of the collar, the collar cannot contact the inner surface of a blood vessel.

OPERATION

Prior to the use of the catheter device of the invention, the location of an undesired material such an occlusion or accumulation of plaque or other lesions within a duct such as a blood vessel of the patient is first determined by conventional techniques including angioscan, X-ray, tomography or the like. Thereafter, an incision can be made in the femoral artery, by way of example, and the filament 24 is then advanced through the artery to the vicinity of the occlusion or accumulation of plaque FIG. 2). In the alternative, access to the region of a blockage can be attained during an operation, such for example, during open-heart surgery. Once the incision is made in the blood vessel in question, known techniques such as those involving fluoroscopy or angioscopy can be used to observe the condition within the blood vessel which is to be treated by use of the catheter device of the invention. In this way, the catheter device is controlled to be advanced into the blood vessel in which the filament has been extended until the region to be treated is reached.

Fluid pressure is then applied to the balloon or bladder 29 of the device in order to position it with respect to the plaque to be removed. In the case of catheter device 20, bladder 29 urges abutments 22 and 23 against the inner surface of the blood vessel 19 and places the device in preparation for the introduction of laser energy. In the case of catheter device 35, inflation of bladder 41 causes standoff 38 as well as the outer surface 36b of the catheter adjacent the standoff to come into contact with the inner surface of the blood vessel, thereby causing the distal end portion of the catheter device 35 to assume a curved position within the blood vessel.

In a case where the blood vessel is totally occluded, it is possible to make use of laser boring catheter 110 (FIGS. 24 and 25) to "notch" out a hole in the undesired material, thereby permitting the use of other catheter devices according to the invention. Where a blood vessel is almost totally occluded by an obstruction such as plaque, but there exists at least a small passage 28a in the obstruction, catheter device 70 (FIGS. 15-17) may be used to bore a hole in the undesired material 28. The passage then enables one of the larger catheter devices of the invention to be advance into a position adjacent the obstruction and to disintegrate the remaining undesired material. This is accomplished by passing filament 74, e.g., guidewire, into the small passage 28a in the undesired material and then rotating catheter device 70 containing fiber optic 73 around the guidewire 74.

Figure 33:
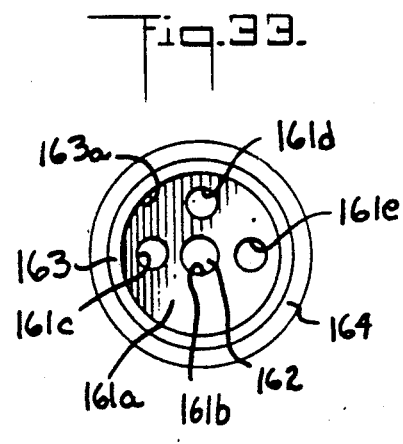
FIG. 33 is an end view of the distal end portion of the catheter of FIG. 32.

With respect to laser boring catheter 161, protective sheath 164 (FIGS. 32 and 33) may be placed over a cylindrical collar 163 to prevent or minimize damage to the blood vessel by the catheter device. Elongated openings in conically shaped distal tip 141 of laser boring catheter 140 (FIGS. 28 and 30) act to prevent the openings from being damaged or clogged by blood or debris from the obstruction disintegrated by laser energy.

When catheter device is used, reduced pressure is applied to suction port 31 in the case of catheter device 20, opening 40a in the case of the catheter device 35, and lumen 81d in the case of catheter 80. Laser energy in the form of pulses, bursts or cycles of application is then applied to either of catheter devices 20, 35 and 80. In the case of device 20, the laser energy vaporizes plaque 28 disposed between the abutment 22 and 23. As the plaque is vaporized, abutment 22 and 23 prevent the escape of laser energy into the blood vessel adjacent the distal end portion of the catheter.

In catheter device 35, the arcuate form of the catheter device, resulting from the inflation of bladder 41, causes the laser energy to be directed toward the center line of the blood vessel (FIG. 9). As a result, the laser energy is dissipated in the central region of the blood vessel as the plaque is vaporized, thereby preventing undesired contact of the laser energy with the inner surface 19a of the blood vessel.

When using catheter device 80, it is possible to detect when the undesired material has been vaporized or otherwise removed from the blood vessel. When the undesired material in the path of laser energy 107 is eliminated, the laser energy strikes the reflective layer 106 of abutment 83b (FIGS. 22 and 23). The laser energy striking reflective layer 106 induces fluorescence or is otherwise reflected back to optical receiving fiber 87 thereby transmitting the reflected energy to the sensor 102, which will signal the operator that the obstruction in the path of laser energy 107 has been removed. Alternatively, the operator of the catheter device of the invention can determine when the procedure of removal of an occlusion or plaque has been completed by fluoroscopic observation or by taking a fluid pressure gradient observation across the lesion. It should be understood that during use of the catheter device of the invention, the blood vessel being treated can remain under observation by known techniques such as the use of an endoscope, angioscan, tomography, X-ray fluoroscope or the like. The catheter device of the invention can be rotated by the operator with respect to the filament during use to effect a sweep of the interior of a blood vessel in carrying out the procedure.

In the catheter device 50, electrically heated element 51 is used to sever undesired material from between abutments 55 and 56. In the catheter device 54, blade 62 is used to sever and release undesired material disposed between abutments 65 and 66.

A soft, conically shaped nose 103 (FIGS. 19, 20, 22 and 23) acts to assist in guiding the catheter device through the blood vessel by reducing the possibility of trauma to the blood vessel, and may be used with any of the catheters of the invention, e.g., catheters 20, 35, 50 and 80, which utilize a chamber between the first and second abutments proximal to the distal tip of the catheter for the elimination of the undesired material.

Occlusion balloon 84 (FIGS. 19, 20 and 21) may be used with any of the catheter devices according to the invention, e.g., catheter devices 20, 35, 50, 70, 80 and 110, when a relatively blood free environment is desired to effectuate removal of the undesired material in the blood vessel. Likewise, radio-opaque bands 104 and 105 (FIG. 20) may be attached to any of the catheter devices according to the invention to facilitate positioning of the catheter device.

For use with any of the catheters according to the invention, an integral spring wire tip 131 (FIG. 27) acts to direct the catheter through the blood vessel and is particularly useful at the branching of a blood vessel. The integral guidewire tip 131 may be used in place of filament or guidewire 85 (FIG. 20).

What is claimed is:

1. A catheter device for use in disintegrating undesired material from a duct within a patient's body comprising:

a catheter having a proximal end portion and a distal end portion adapted to be inserted within a duct in the patient's body;

means disposed adjacent the distal end portion of the catheter for intersecting and releasing undesired material from the interior of the duct in the patient's body when the distal end portion of the catheter is disposed adjacent to the undesired material, the intersecting and releasing means including the catheter having an open chamber disposed therein and formed by a bottom wall portion extending along the length of the catheter and a first abutment and a second abutment extending radially from the outer surface of the catheter to opposite end portions respectively of the bottom wall portion, the first abutment and the second abutment being spaced apart from one another along the length of the catheter with the second abutment disposed adjacent the distal end portion of the catheter, the first and second abutments being adapted to have the open chamber therebetween disposed adjacent to the inner surface of the duct for receiving undesired material therein when an outer portion of each of the first and second abutments is urged against the inner surface of the duct, and a fiber optic extending within the interior of the catheter from the proximal end portion thereof to the chamber for delivering laser energy into the chamber and toward the second abutment when the fiber optic is connected to a source of laser energy, the second abutment when intercepting laser energy from the fiber optic which has passed through the chamber preventing the laser energy from impinging on the inner surface of the duct and reflecting at least a portion of the laser energy intercepted thereby as the undesired material is disintegrated;

an additional fiber optic extending within the interior of the catheter from the proximal end portion thereof to the chamber to receive light energy emitted from the second abutment in response to laser energy directed thereto as the undesired material is disintegrated; and means connected to the second fiber optic for enabling the emitted light energy to be sensed to permit determining the extent of disintegration of the undesired material.

2. A catheter device in accordance with claim 1 and further comprising means disposed on the second abutment and facing the chamber for emitting a predetermined wavelength of light energy in response to laser energy directed to the second abutment as the undesired material disintegrates.

3. A catheter device in accordance with claim 2 in which the means for emitting a predetermined wavelength of light energy comprises fluorescent material disposed on the second abutment.

4. A catheter device in accordance with claim 3 in which the fluorescent material is conditioned to emit a multiple of the level of light being applied thereto for enhancing detection of the light transmitted by the fiber optic.

5. A device in accordance with claim 1 and further comprising:

an inflatable bladder mounted on the catheter adjacent the distal end portion thereof substantially opposite the chamber formed by the first and second abutments; and means extending through the length of the catheter and connected to the bladder for controllably inflating the bladder when the device is disposed in the duct to enable the inflated bladder to contract the inner surface of the duct and urge the distal end portion of the catheter including the outer portion of each of the first and second abutments, against the inner surface of the duct adjacent thereto, whereby the chamber is positioned adjacent to the inner surface of the duct and the undesired material therein.

6. A catheter device in accordance with claim 1 in which the catheter has a lumen extending throughout the length thereof and further comprising a filament extending along the length of the lumen to adjacent the distal end portion of the catheter, the catheter being adapted to be translated and rotated with respect to the filament, whereby the catheter is adapted to be positioned and rotated within the duct.

7. A catheter device in accordance with claim 1 and further comprising an occluding balloon surrounding the catheter adjacent the chamber formed by the first and second abutments; and means extending throughout the length of the catheter and connected to the occluding balloon for controllably inflating the occluding balloon when the device is disposed in the duct to enable the occluding balloon when inflated to contact the inner surface of the duct and to cut off substantially the flow of blood proximal to the distal end portion of the catheter.

8. A catheter device in accordance with claim 1 and further comprising:

radio-opaque bands disposed adjacent to the chamber formed by the first and second abutments which absorb or block X-ray radiation when an X-ray fluoroscope is used to guide the chamber to adjacent an occlusion.

9. A catheter device in accordance with claim 1 and in which the catheter includes an aspirating lumen extending through the length of the catheter to the chamber and connected to the chamber, the aspirating lumen being adapted to aspirate and remove undesired material from the chamber.

10. A catheter device in accordance with claim 1 and in which the catheter includes an irrigation lumen extending through the length thereof and connected to the chamber, the irrigation lumen being adapted to deliver a liquid to the chamber for irrigating the chamber and a portion of the interior of the duct adjacent thereto.

11. A catheter device in accordance with claim 1 and further comprising a conically shaped nose of soft or compliant material, the conically shaped nose having a base portion thereof disposed at the distal end portion of the catheter device.

12. A catheter device according to claim 1, the catheter having an irrigation lumen extending along the length thereof from the proximal end portion to the open chamber for delivering liquid to a portion of the duct adjacent to the open chamber for the purpose of irrigation, an inflatable bladder mounted on the catheter proximal to the distal end portion of the catheter, and means for controllably inflating the bladder when the device is disposed in the duct to enable the inflated bladder to contact the inner surface of the duct and urge the catheter against the inner surface of the duct substantially opposite to the bladder, whereby the laser energy is adapted to cause excision of undesired material within the duct when the distal end portion of the catheter is disposed proximal to an obstruction in the duct.

13. A catheter device in accordance with claim 12 in which the catheter includes an aspirating lumen extending from the proximal end portion to the open chamber for the removal of undesired material from a portion of the duct adjacent to the open chamber.

14. A catheter device in accordance with claim 13 wherein a filament extends along the length of the aspirating lumen to adjacent the distal end portion of the catheter, the catheter being adapted to be translated and rotated with respect to the filament, such that the catheter is adapted to be positioned on rotated within the duct.

15. A catheter device in accordance with claim 12 in which the catheter includes an aspiration lumen for aspirating liquid and materials from the duct.

16. A catheter device in accordance with claim 12 and further comprising an occluding balloon surrounding the catheter adjacent the distal end portion thereof; and means extending through the length of the catheter for controllably inflating the occluding balloon when the device is disposed in the duct to enable the inflated occluding balloon to contact the inner surface of the duct, thereby serving to substantially cut off the flow of blood proximal to the distal end portion of the catheter.

17. A catheter device in accordance with claim 12 and further comprising:

one or more radio-opaque bands on the distal end portion of the catheter which absorb or block x-ray radiation when and x-ray fluoroscope is used to guide the open chamber to a position in the duct adjacent to undesired material.

18. A method for removing undesired material from a duct within a patient's body by use of a catheter capable of transmitting laser energy, the catheter having a proximal end portion and a distal end portion, said distal end portion being adapted to be inserted within a duct in the patient's body, the catheter having means disposed adjacent the distal end portion of the catheter for intersecting and releasing undesired material from the interior of the duct when the distal end portion of the catheter is disposed adjacent to the undesired material, said means comprising the catheter having an open chamber disposed therein and formed by a bottom wall portion extending along the length of the catheter and a first and a second abutment extending radially from respective outer portions that intersect the outer surface of the catheter to opposite end portions respectively of the bottom wall portion, the first abutment and the second abutment being spaced apart from one another along the length of the catheter with the second abutment disposed adjacent the distal end portion thereof, the first and second abutments being adapted to have the open chamber therebetween disposed adjacent to the inner surface of the duct for receiving undesired material therein when the outer portion of each of the first and second abutments is adjacent the inner surface of the duct with the second abutment being adapted to reflect at least a portion of the laser energy intercepted thereby as the undesired material is disintegrated, a fiber optic extending with the interior of the catheter from the proximal end portion thereof to between the first and second abutments to deliver laser energy across the chamber formed by the first and second abutments and toward the second abutment adjacent the distal end portion of the catheter when the fiber optic is connected to a source of laser energy, said chamber being capable of preventing the escape of laser energy applied in the chamber, and an additional fiber optic extending within the interior of the catheter from the proximal end portion thereof to the chamber to receive light energy emitted from the second abutment in response to laser energy directed thereto as the undesired material is disintegrated, an inflatable bladder mounted on the catheter adjacent the distal end portion thereof disposed substantially opposite the intersecting and releasing means;

the method comprising the steps of placing the distal end portion of the catheter adjacent the undesired material;

controllably inflating the bladder when the distal end portion of the catheter is adjacent the undesired material to enable the inflated bladder to contact the inner surface of the duct and urge the distal end portion of the catheter against the inner surface of the duct adjacent thereto;

positioning the chamber adjacent to the undesired material, operating the means of intersecting and releasing the undesired material when positioned adjacent to the inner surface of the duct at the undesired material, and sensing the light energy received by the additional fiber optic, the light energy being indicative of the state of the releasing of the undesired material from the duct.

19. The method according to claim 18 and further comprising the step of preventing the flow of blood through the duct by means of an occluding balloon mounted on the catheter proximal to the inflatable bladder which contacts the inner surface of the duct.

20. A method for removing undesired material from an interior surface of a blood vessel within a patient's body by use of a catheter having a proximal end portion and a distal end portion, said distal end portion adapted to be inserted within a blood vessel in the patient's body, the catheter having means disposed adjacent the distal end portion of the catheter for intersecting and releasing undesired material from the interior of the blood vessel when the distal end portion of the catheter is disposed adjacent to the undesired material, an inflatable bladder mounted on the catheter adjacent the distal end portion thereof; the catheter further including an irrigation lumen extending through the length of the catheter for passing a flow of irrigation liquid to the distal end portion of the catheter, and a fiber optic to deliver laser energy extending within the interior of the catheter from the proximal end portion thereof to the distal end portion of the catheter;

the method comprising the steps of inserting the distal end portion of the catheter into a blood vessel of the patient; placing the distal end portion of the catheter adjacent the undesired material; controllably inflating the bladder when the distal end portion of the catheter is adjacent the undesired material to enable the inflated bladder to contact the inner surface of the blood vessel and to urge the distal end portion of the catheter against the inner surface of the blood vessel adjacent thereto so as to immobilize the distal end portion of the catheter on the blood vessel;

applying laser energy to the undesired material to release the material from the interior surface of the blood vessel without permitting the laser energy to impinge on the inner surface of the blood vessel; and delivering the irrigation liquid from the distal end portion of the catheter toward the undesired material to facilitate the release thereof from the blood vessel.

21. The method according to claim 20 and further comprising the step of preventing the flow of blood through the blood vessel by an occluding balloon mounted on the catheter proximal to the inflatable bladder which contacts the inner surface of the blood vessel.

22. A catheter device for use in removing undesired material from a duct within a patient's body comprising a catheter having a proximal end portion and a distal end portion adapted to be inserted within a duct in the patient's body;

means disposed adjacent the distal end portion of the catheter for intersecting and releasing undesired material from the interior of the duct in a patient's body when the distal end portion of the catheter is disposed adjacent to the undesired material, said means comprising the catheter having an open chamber disposed therein and formed by a bottom wall portion extending along the length of the catheter and a first and a second abutment extending radially from respective outer portions of the abutments that intersect the outer surface of the catheter to opposite end portions respectively of the bottom wall portion, the first abutment and the second abutment being spaced apart from one another along the length of the catheter with the second abutment disposed adjacent the distal end portion thereof, the first and second abutments being adapted to have the open chamber therebetween disposed adjacent the inner surface of the duct for receiving undesired material therein when the outer portion of each of the first and second abutments is urged against the inner surface of the duct, and a fiber optic extending within the interior of the catheter from the proximal end portion thereof to between the first and second abutments to deliver laser energy across the chamber formed by the first and second abutments and toward the second abutment adjacent the distal end portion of the catheter when the fiber optic is connected to a source of laser energy, the second abutment preventing the laser energy from impinging on the inner surface of the duct, an inflatable bladder mounted on the catheter adjacent the distal end portion thereof disposed substantially opposite the intersecting and releasing means, and means for controllably inflating the bladder when the device is disposed in the duct to enable the inflated bladder to contact the inner surface of the duct and to urge the distal end portion of the catheter, including the first and second abutments, against the inner surface of the duct adjacent thereto, whereby the means for intersecting the releasing the undesired material is positioned adjacent to the inner surface of the duct.

23. A catheter device in accordance with claim 22 and further comprising a lumen having a proximal end and distal end disposed within the catheter, the proximal end of the lumen being adapted to be connected to a source of reduced pressure less than the ambient pressure, the distal end of the lumen having a port disposed adjacent to the distal end portion of the catheter, the portion being adapted to receive undesired material when connected to the source of reduced pressure.

24. A catheter device in accordance with claim 22 and further comprising a filament extending along the length of the catheter to adjacent the distal end portion of the catheter, the catheter being rotatably disposed about the filament and adapted to be translated and rotated with respect to the filament, whereby the catheter is adapted to be positioned and to be rotated within a duct.

25. A laser angioplasty catheter device comprising a catheter having a proximal end portion and a distal end portion adapted to be inserted within a blood vessel, the catheter having an open chamber disposed therein and formed by a bottom wall portion extending along the length of the catheter and a first and a second abutment extending radially from respective outer portions of the abutments that intersect the outer surface of the catheter to opposite end portions respectively of the bottom wall portion, the first abutment and the second abutment being spaced apart from one another along the length of the catheter with the second abutment adjacent the distal end portion thereof, the first and second abutments being adapted to have the open chamber therebetween disposed adjacent the inner surface of the blood vessel for receiving undesired material therein when the outer portion of each of the first and second abutments is adjacent the inner surface of the blood vessel, and a fiber optic extending within the interior of the catheter from the proximal end portion thereof to between the first and second abutments to deliver laser energy across the chamber formed by the first and second abutments and toward the second abutment adjacent the distal end portion of the catheter when the fiber optic is connected to a source of laser energy, said chamber being capable of preventing the escape of laser energy applied in the chamber, whereby the laser energy is adapted to cause excision of material within the blood vessel when disposed between the first and second abutments with the second abutment adjacent the distal end portion of the catheter blocking the laser energy from intersecting the inner wall of the blood vessel.

26. A laser angioplasty device in accordance with claim 25 in which the fiber optic terminates adjacent to a portion of the first abutment facing the second abutment that is adjacent the distal end portion of the catheter.

27. A laser angioplasty device in accordance with claim 26 and further comprising means connected to the fiber optic for directing laser energy from adjacent the first abutment and across the chamber toward the second abutment adjacent the distal end portion of the catheter.

28. A laser angioplasty device in accordance with claim 27 in which the means for directing the laser energy comprises means for refracting the laser energy.

29. A laser angioplasty device in accordance with claim 25 and further comprising a lumen having a proximal end and a distal end disposed within the catheter, the proximal end of the lumen being adapted to be connected to a source of reduced pressure less than the ambient pressure, the distal end of the lumen having a port communicating with the chamber formed between the first and second abutments, the port being adapted to receive material subjected to laser energy from between the first and second abutments when connected to the source of reduced pressure.

30. A laser angioplasty device in accordance with claim 25 further comprising an inflatable bladder mounted on the catheter adjacent a portion thereof disposed substantially opposite to the first and second abutments, and means for controllably inflating the bladder when the device is disposed in a blood vessel to enable the inflated bladder to contact the inner surface of the blood vessel adjacent thereto, whereby the chamber between the first and second abutments is covered by the inner surface of the blood vessel.

31. A laser angioplasty device in accordance with claim 30 in which the means for controllably inflating the bladder comprises a lumen having a proximal end and a distal end, the lumen extending within the catheter and having its distal end connected to the bladder, the proximal end of the lumen being adapted for connection to a source of fluid pressure for inflating the bladder.

32. A laser angioplasty device in accordance with claim 25 and further comprising a filament extending along the length of the catheter to adjacent the distal end portion of the catheter, the catheter being rotatably disposed about the filament and adapted to be translated and rotated with respect to the filament, whereby the catheter is adapted to be positioned and to be rotated within a blood vessel.

33. A method for removing undesired material from a duct within a patient's body by use of a catheter having a proximal end portion and a distal end portion, sand distal end portion adapted to be inserted within a duct in the patient's body, the catheter having means disposed adjacent the distal end portion of the catheter for intersecting and releasing undesired material from the interior of the duct in a patient's body when the distal end portion of the catheter is disposed adjacent to the undesired material, and an inflatable bladder mounted on the catheter adjacent the distal end portion thereof disposed substantially opposite the intersecting and releasing means;

the method comprising the steps of placing the distal end portion of the catheter adjacent the undesired material;

controllably inflating the bladder when the distal end portion of the catheter is adjacent the undesired material to enable the inflated bladder to contact the inner surface of the duct and urge the distal end portion of the catheter against the inner surface of the duct adjacent thereto; and operating the means for intersecting and releasing undesired material when positioned adjacent to the inner surface of the blood vessel at the undesired material, said means including the catheter having an open chamber disposed therein and formed by a bottom wall portion extending along the length of the catheter and a first and second abutment extending radially from respective outer portions of the abutments that intersect the outer surface of the catheter to opposite end portions of the bottom portion, the first abutment and the second abutment being spaced apart from one another along the length of the catheter with the second abutment disposed adjacent the distal end portion thereof, the first and second abutments being adapted to having the open chamber therebetween disposed adjacent to the inner surface of the duct for receiving undesired material therein when the outer portion of each of the first and second abutments is adjacent the inner surface of the duct, and a fiber optic extending within the interior of the catheter from the proximal end portion thereof to between the first and second abutments to deliver laser energy across the chamber formed by the first and second abutments and toward the second abutments adjacent the distal end portion of the catheter when the fiber optic is connected to a source of laser energy, said chamber being capable of preventing the escape of laser energy applied in the chamber.

34. A method of removing undesired material from a duct within a patient's body by use of a catheter having a proximal end portion and a distal end portion adapted to be inserted within a duct, the catheter having an open chamber disposed therein and formed by a bottom wall portion extending along the length of the catheter and a first and a second abutments extending radially from respective outer portions of the abutments that intersect the outer surface of the catheter to opposite end portions respectively of the bottom wall portion, the first abutment and the second abutment being spaced apart from one another along the length of the catheter adjacent the distal end portion thereof, with the second abutment being adjacent the distal end portion of the catheter, the first and second abutments being adapted to have the open chamber therebetween disposed adjacent the inner surface of the duct for receiving undesired material therein when the outer portion of each of the first and second abutments is adjacent the inner surface of the duct, and a fiber optic extending within the interior of the catheter from the proximal end portion thereof to between the first and second abutments to deliver laser energy across the chamber formed by the first and second abutments and toward the second abutment adjacent the distal end portion of the catheter when the fiber optic is connected to a source of laser energy, the method comprising the steps of positioning the chamber formed between the first and second abutments adjacent the undesired material within the duct, and applying laser energy emitted from the fiber optic into the undesired material in the chamber to excise the material, the second abutment adjacent the distal end of the catheter absorbing any laser energy impacting thereon.

35. A laser angioplasty catheter device comprising a catheter having a proximal end portion and a distal end portion adapted to be inserted within a duct, the catheter including having an open chamber disposed therein formed by a bottom wall portion extending along the length of the catheter and a first and second abutment extending radially from respective outer portions of the abutments that intersect the outer surface of the catheter opposite end portions respectively of the bottom wall portion, the first abutment and the second abutment being spaced apart from one another along the length of the catheter adjacent the distal end portion thereof with the second abutment being adjacent the distal end portion of the catheter, the first and second abutments being adapted to have the open chamber therebetween disposed adjacent to an inner surface of the duct for receiving undesired material therein when the outer portion of each of the first and second abutments are adjacent the inner surface of the duct, a fiber optic extending within the interior of the catheter from the proximal end portion thereof to between the first and second abutments to deliver laser energy across the chamber formed by the first and second abutments and toward the second abutment adjacent the distal end portion of the catheter when the fiber optic is connected to a source of laser energy, said chamber being capable of preventing the escape of laser energy applied in the chamber, an inflatable bladder mounted on the catheter adjacent a portion thereof disposed substantially opposite to the first and second abutments, and means for controllably inflating the bladder when the device is disposed in a duct to enable the inflated bladder to contact the inner surface of the duct and to urge the first and second abutments against the inner surface of the duct adjacent thereto such that the open chamber between the pair of abutments is covered by the inner surface of the duct, whereby the laser energy is adapted to cause excision of material within the duct when disposed between the first and second abutments within the second abutment adjacent the distal end portion of the catheter blocking the laser energy from intersecting the inner wall of the duct.

36. A laser angioplasty device in accordance with claim 35 in which the means for controllably inflating the bladder comprises a lumen having a proximal end portion and a distal end portion extending within the catheter and having its distal end portion connected to the bladder, the proximal end portion of the lumen being adapted for connection to a source of fluid pressure for inflating the bladder.

* * * * *